（12) United States Patent
Kawazoe et al.

(10) Patent No.: US 7,195,699 B2
(45) Date of Patent: Mar. 27, 2007

(54) ELECTROPHORESIS MEMBER, PRODUCTION THEREOF AND CAPILLARY ELECTROPHORESIS APPARATUS

(75) Inventors: Hiroshi Kawazoe, Shimodate (JP);
Tomoyuki Kamata, Shimodate (JP);
Atsushi Takahashi, Shimodate (JP);
Tsuyoshi Sonehara, Kokubunji (JP);
Tatemi Ido, Kodaira (JP); Kunio Harada, Hachiouji (JP)

(73) Assignees: Hitachi Chemical Co., Ltd., Tokyo (JP); Hitachi, Ltd., Tokyo (JP)

( * ) Notice: Subject to any disclaimer, the term of this patent is extended or adjusted under 35 U.S.C. 154(b) by 775 days.

(21) Appl. No.: 10/628,274

(22) Filed: Jul. 29, 2003

(65) Prior Publication Data

US 2004/0035702 A1 Feb. 26, 2004

(30) Foreign Application Priority Data

Aug. 26, 2002 (JP) ............................. 2002-244676

(51) Int. Cl.
*G01N 27/447* (2006.01)
*G01N 27/453* (2006.01)

(52) U.S. Cl. ................. 204/603; 204/452; 204/453; 204/604; 264/139; 264/154

(58) Field of Classification Search ................ 204/452, 204/453, 603, 604; 264/139, 154
See application file for complete search history.

(56) References Cited

U.S. PATENT DOCUMENTS 6,048,444 A * 4/2000 Takahashi et al. .......... 204/603
6,063,251 A * 5/2000 Kane et al. .................. 204/601
6,977,034 B2 * 12/2005 Morioka et al. ............ 204/603

FOREIGN PATENT DOCUMENTS

JP      2000-131278 A  *  5/2000
JP      2001-264293       9/2001
JP      2001-324475       11/2001

* cited by examiner

*Primary Examiner*—Kaj K. Olsen
(74) *Attorney, Agent, or Firm*—Antonelli, Terry, Stout and Kraus, LLP.

(57) ABSTRACT

An electrophoresis member is produced by laying a plurality of capillaries on an adhesive layer born on a support layer to form a capillary layer, laminating thereon a second support layer, and partially removing the first support layer, the first adhesive layer and the second support layer to partially expose the capillaries to form a window portion for irradiation and detection and a sample injection portion for injecting a sample.

14 Claims, 8 Drawing Sheets

ELECTROPHORESIS MEMBER, PRODUCTION THEREOF AND CAPILLARY ELECTROPHORESIS APPARATUS

BACKGROUND OF THE INVENTION (a) Field of the Invention

The present invention relates to an electrophoresis apparatus used for analyzing polymers, such as DNA, RNA and proteins, particularly, an electrophoresis member used in DNA sequencers, and to its production (b) Description of the Related Art According to one technique of DNA sequencing, a liquid containing DNA fragments is separated by electrophoresis to detect the fluorescence of each DNA fragment. A conventional method is a slab gel electrophoresis method wherein electrophoresis is conducted in a gel filled between glass plates. Decreased gel thickness and higher voltage are necessary to speed up the electrophoresis separation, but generation of heat has limited the applicable voltage.

A new technique is a capillary electrophoresis method using quartz capillaries of about 10 to 100 µm in inside diameter. Because capillaries decrease the generation of heat, higher voltage can be applied as compared with the slab gel electrophoresis method, increasing the separation speed more than 10 times. At present full automatic multi-capillary system using a capillary array of from several to 100-capillaries-alignment is employed actively.

The multi-capillary array system needs special designs to irradiate a plurality of capillaries with light for exciting fluorescence. There have been developed various systems including beam scanning system, beam spreading system and multi-light source system, which however involve the problems of low irradiation efficiency, low analyzing sensitivity and high cost for a plurality of light sources. A solution disclosed in Japanese Patent Application Non-examined Publication No. H09-96623 (1997) is irradiating light perpendicularly to the capillaries, on a plane wherein a plurality of capillaries are aligned, to irradiate all capillaries with one beam using the lens effects of the capillaries. This system, called multiple focusing system, enables highly sensitive analysis with only one light source.

Another method recently attracting attentions is the chip capillary electrophoresis method disclosed in the specification of U.S. Pat. No. 5,958,694, whereby electrophoresis is conducted through channels (capillaries) of about 10 µm wide and deep made on a surface of a glass or quartz plate by etching or the like. The substrate used is sometimes called an electrophoresis chip. Compared with the conventional capillaries, the electrophoresis chip has the advantage of higher heat releasing effect, enabling production of short, high-density channel arrays. The method, however, is not suit to rapid analysis of a large quantity of sample, because the sample has to be transferred from reaction tubes to the chip by hand labor (pipetting).

Conventionally, capillary arrays have been assembled by bundling capillaries using one assembling jig for every capillary. As the number of capillaries increases, the bundle of capillaries becomes bulky, requiring a large space in an apparatus and making downsizing the apparatus difficult. Further, not only the steps and time of capillary array assembling but also troubles such as the breakage of capillaries are increased. Additionally, in the assembled arrays, most parts of the capillaries are exposed in the air, so that they are easily broken on handling and cannot release heat efficiently due to the air surrounding them. In Japanese Patent Application Unexamined Publication Nos. 2001-264293 and 2001-324475 is disclosed a capillary array wherein the sample injection parts and detection parts of a plurality of capillaries are aligned in parallel by penetrating the capillaries through a box-like load header near the sample injection parts and penetrating the detection parts between two support plates. The most parts of the capillaries of the array are also exposed in the air. Therefore, the capillaries are easily broken on handing and cannot release heat efficiently.

SUMMARY OF THE INVENTION

An object of the present invention is to provide an electrophoresis member that has an accurate, compact capillary array, is easy to handle and has high heat releasability. Another object of the invention is to provide an efficient method of producing the electrophoresis member.

In one aspect of the invention, there is provided an electrophoresis member, comprising a plurality of capillaries and a first supporter comprising a first support layer, a first adhesive layer and a second support layer, wherein:

the first adhesive layer is positioned on the first support layer, the capillaries lie on the first adhesive layer to form a capillary layer, and the second support layer is positioned on the capillary layer;

the capillary layer has a window portion and a sample injection portion including a terminating end of each capillary, the capillaries, at the sample injection portion, being exposed by partially removing one end portion of the first supporter and, at the window portion, being exposed by partially removing another portion of the first supporter;

the capillaries, at each of the window portion and the sample injection portion, are arranged so that axes of the capillaries have a parallel, coplanar relationship;

the capillaries have, in the window portion, detection parts defined as intersections of the capillaries and a plane intersecting perpendicularly to the axes of the capillaries; and the capillaries have equal lengths between the detection parts and the terminating ends included in the sample injection portion.

In a further aspect of the invention, the capillaries are glass capillaries.

In a still further aspect of the invention, the first supporter has a second adhesive layer interposed between the capillary layer and the second support layer.

In a still further aspect of the invention, each capillary, except the window portion or a part of the window portion including the detection part, has a coating layer as an outermost layer.

In a still further aspect of the invention, the capillaries, at the sample injection portion, are arranged at equal intervals given by dividing 9 mm by an integer.

In a still further aspect of the invention, the capillaries, in the window portion, are supported before and behind the detection parts by a second supporter.

In a still further aspect of the invention, the first supporter has an opening including the window portion.

In a still further aspect of the invention, there is provided a method of producing an electrophoresis member, comprising steps (1), (2) and (3):

(1) a step of forming a capillary layer comprising a plurality of capillaries on an adhesive layer born on a first support layer, by laying the capillaries on the adhesive layer by using a numerically controlled laying apparatus, so that the capillary layer has a window portion and a sample injection portion including a terminating end of each capillary, the capillaries, at each of the window portion and the sample injection portion, being arranged so that axes of the capillaries have a parallel, coplanar relationship;

the capillaries have, in the window portion, detection parts defined as intersections of the capillaries and a plane intersecting perpendicularly to the axes of the capillaries; and the capillaries have equal lengths between the detection parts and the terminating ends included in the sample injection portion;

(2) a step of laminating a second support layer on the capillary layer; and (3) a step of exposing the capillaries, at each of the window portion and the sample injection portion, by partially removing the first support layer, the first adhesive layer and the second support layer.

In a still further aspect of the invention, the second support layer used in the above-mentioned method bears on one surface a second adhesive layer, and is laminated on the capillary layer, so that the second adhesive layer contacts the capillary layer, and, in step (3), the capillaries, at each of the window portion and the sample injection portion, are exposed by partially removing the first support layer, the first adhesive layer, the second adhesive layer and the second support layer.

In a still further aspect of the invention, the capillaries used in the above-mentioned method are glass capillaries.

In a still further aspect of the invention, each capillary used in the above-mentioned method is a glass capillary having a coating layer as an outermost layer, and the method further comprises a step of peeling off the coating layer at the window portion or at a part of the window portion including the detection parts.

In a still further aspect of the invention, the capillaries are applied with a load while being laid on the first adhesive layer.

In a still further aspect of the invention, the first adhesive layer and/or the capillaries are applied with energy convertible into heat while being laid on the first adhesive layer.

In a still further aspect of the invention, there is provided a capillary electrophoresis apparatus, comprising the electrophoresis member of the invention and a means for reflecting a laser ray in the opening to irradiate the laser ray to the detection parts of the capillaries through a plane parallel to the plane wherein the axes of the capillaries lie in parallel.

DESCRIPTION OF THE PREFERRED EMBODIMENTS

Figure 1:
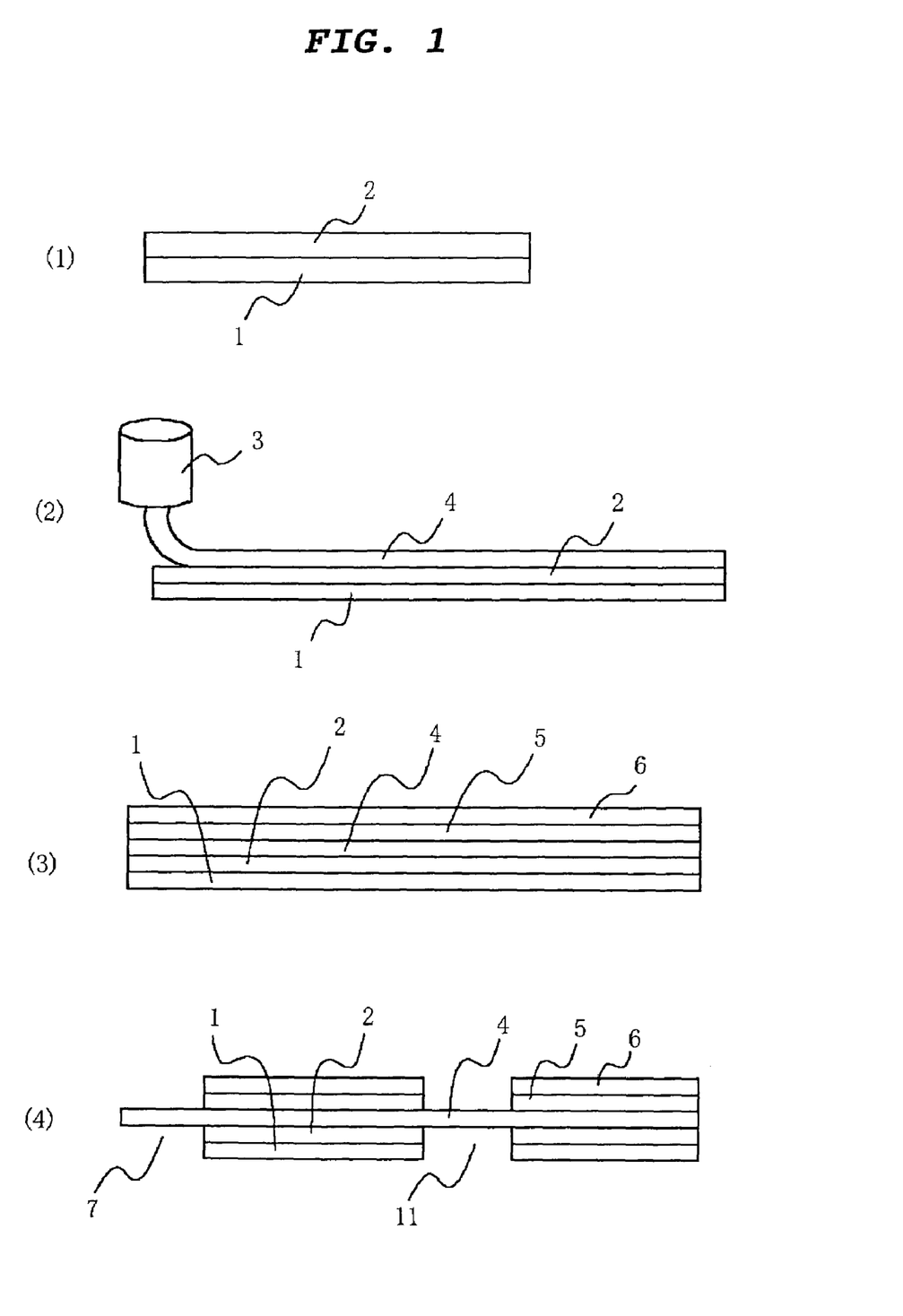
FIG. 1 is a side view illustrating a production process of an embodiment according to the invention.
Figure 2:
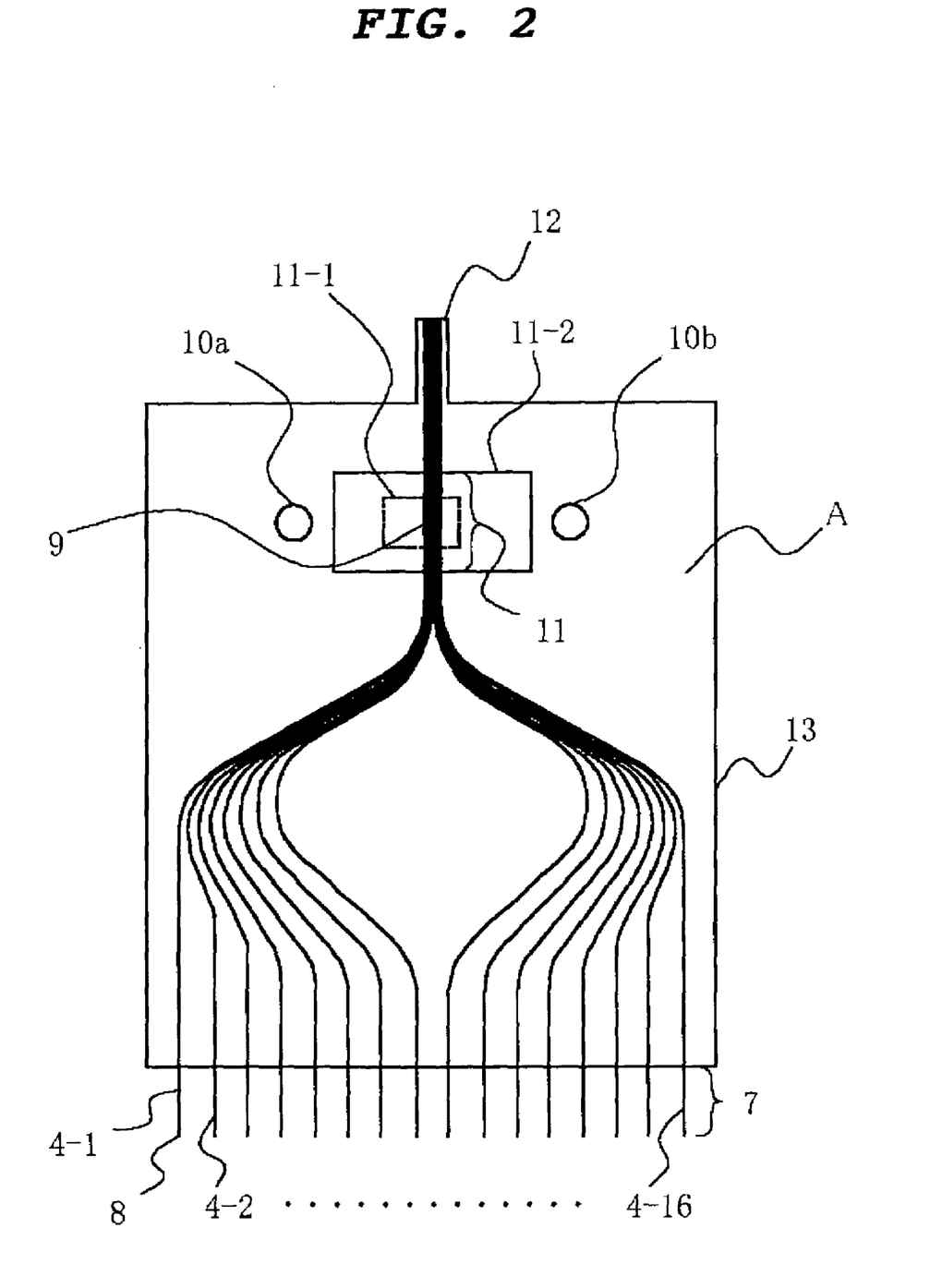
FIG. 2 is an elevation of an electrophoresis member of an embodiment according to the invention, which is obtainable by the process of FIG. 1 followed by outside machining.
Figure 3:
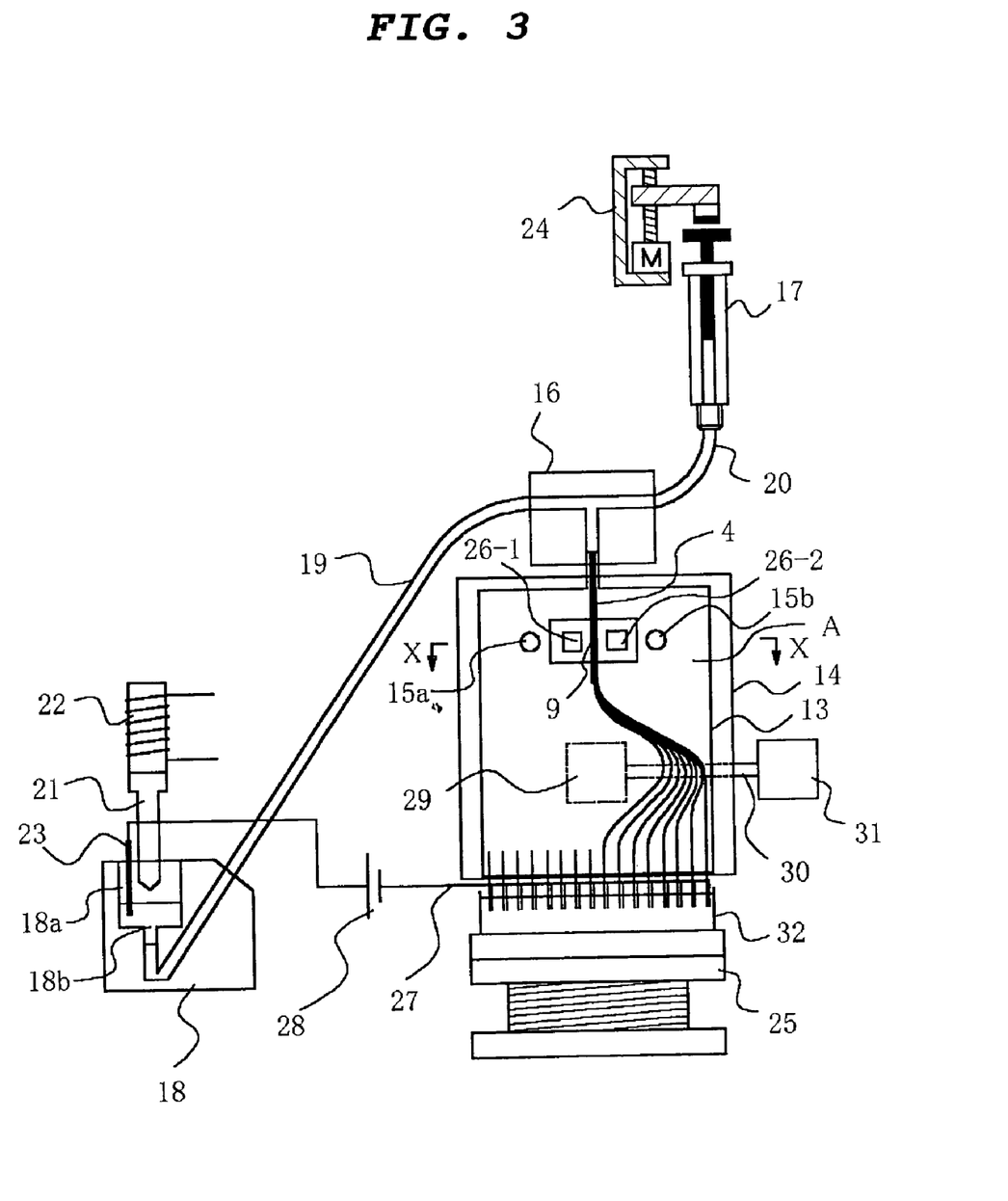
FIG. 3 is an elevation illustrating an electrophoresis apparatus wherein the electrophoresis member of FIG. 2 is assembled.
Figure 7:
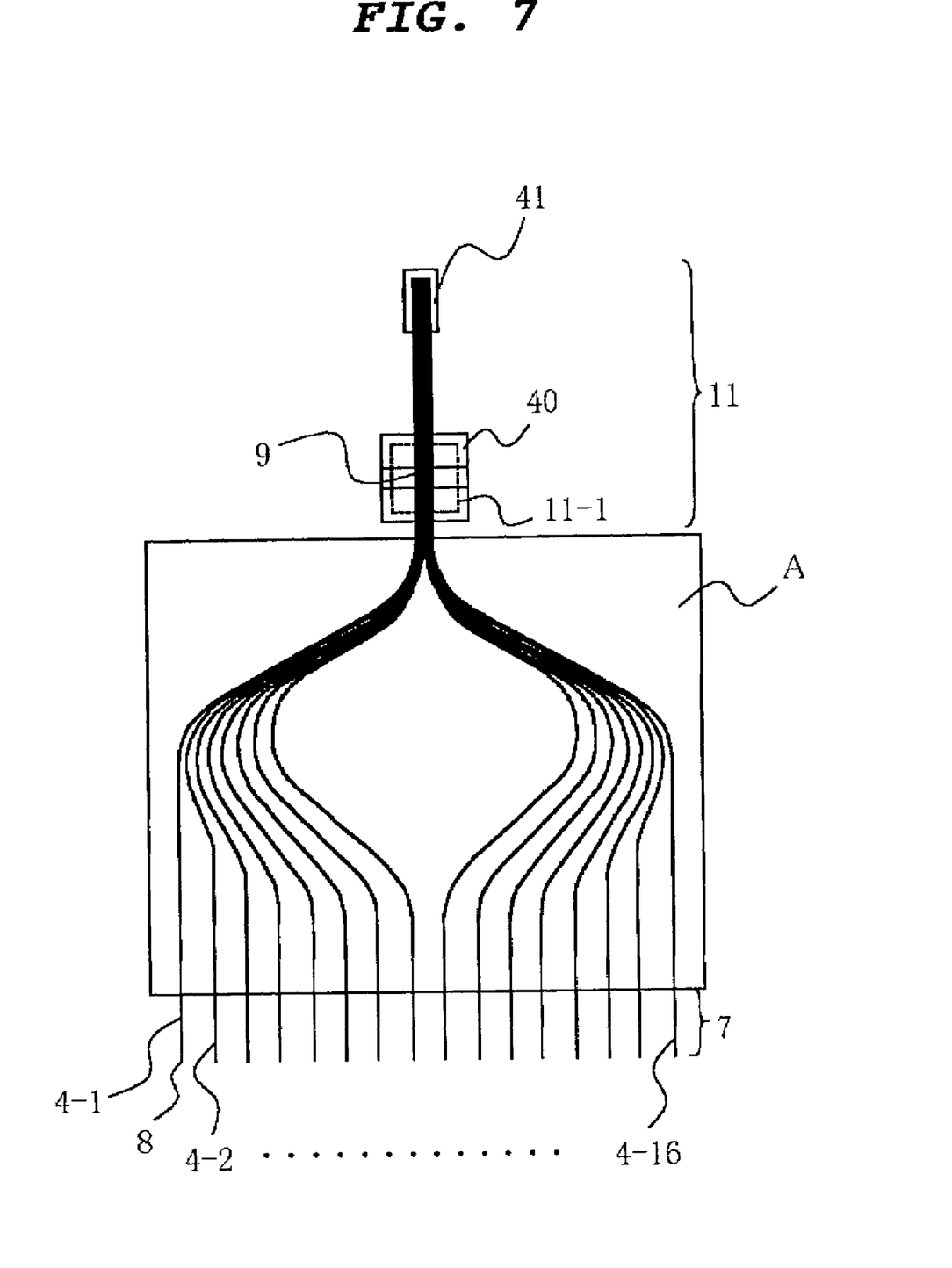
FIG. 7 is an elevation of the electrophoresis member produced in Example 2.

FIG. 1 shows an illustration of the production process and layer structure of the electrophoresis member of the invention, FIG. 2 shows an elevation of an electrophoresis member of an embodiment according to the invention, and FIG. 7 shows an elevation of another embodiment. In FIGS. 2, 3 and 7, to show the array of capillaries, a part or all of the unexposed portions of the capillaries are also shown with full lines.

The electrophoresis member of the invention comprises a plurality of capillaries and a first supporter comprising a first support layer, a first adhesive layer and a second support layer. The first adhesive layer is positioned on the first support layer, and the capillaries lie on the first adhesive layer to form a capillary layer. The second support layer is positioned on the capillary layer. As shown in FIG. 1(4), the first supporter of the electrophoresis member of the invention may comprise a first support layer 1, a first adhesive layer 2, a second adhesive layer 5 and a second support layer 6, so that the second adhesive layer 5 is positioned on a capillary layer comprising a plurality of capillaries 4 lying on the first adhesive layer 2, and the second support layer 6 is positioned on the second adhesive layer 5. The capillary layer comprising the capillaries 4 has a sample injection portion 7 and a window portion 11. The capillaries 4, at the sample injection portion 7, are exposed by partially removing one end portion of the first supporter comprising the first support layer 1, the first adhesive layer 2, the second adhesive layer 5 and the second support layer 6, and, at the window portion 11, are exposed by partially removing another portion of the first supporter. The sample injection portion 7 includes one terminating end of every capillary 4. The capillaries 4, at each of the window portion 11 and the sample injection portion 7, are arranged so that the axes of the capillaries 4 have a parallel, coplanar relationship. The capillaries 4, at the window portion 11, are arranged in parallel with neighboring capillaries contacting each other, and, at the sample injection portion 7, in parallel at equal intervals. In the window portion 11, the capillaries 4 have detection parts 9 defined as intersections of the capillaries and a plane intersecting perpendicularly to the axes of the capillaries 4. The capillaries 4 are transparent, at least, at the detection parts 9 or at the detection parts 9 and their vicinities because a laser ray is irradiated to the detection parts 9.

For example, the first supporter may support the capillaries only between the window portion and the sample injection part, or as shown in FIG. 2, the capillaries 4 may be exposed at the window portion 11 by making an opening 11-2 by partially removing the first supporter A. In either case, in the window portion 11, the capillaries 4 may be supported before and behind the detection parts by a second supporter 40.

Non limitative but preferred shapes of the first support layer 1 and the second are plate-like shapes 20 to 100 μm in thickness. The materials of the first support layer 1 and the second support layer 6 depend on the application. Examples of good, electrical insulators are plates used in printed wiring boards, for example, epoxy resin plates and polyimide resin plates, and film used in flexible printed wiring boards, for example, polyimide film such as CAPTON (Trade name) film produced by E. I. Du Pont de Nemours and Company, polyethylene terephthalate (PET) films such as TETRON (Trade name) film produced by Teijin Ltd., and polyphenylene sulfide (PPS) film such as TORERINA (Trade name) produced by Toray Industries, Inc. Examples of materials with high heat-releasability are metal plates, such as aluminum, copper and SUS, glass plates and quartz plates. The surfaces of metal plates are preferably covered with a resin coating layer of an electrically insulating resin, such as epoxy resin, polyimide resin and silicone resin.

A suitable example of the second supporter 40 is a V-grooved substrate, which is a bloc, such as a quartz, glass, SUS or plastic bloc, having parallel V-grooves on one surface. The capillaries can be kept in parallel at equal intervals by equalizing the intervals of the V-grooves to those of the capillaries and inlaying the capillaries in the V-grooves individually.

The first adhesive layer 2 and the second adhesive layer 5 are preferably formed of a tacky adhesive, for example, polyisobutylene such as BISTANEX MML-120 (Trade name, produced by Tornex Co., Ltd.), acrylonitrile-butadiene rubber, such as NIPOL N1432 (Trade name, produced by Nippon Zeon Co., Ltd.), and chlorosulfonated polyethylene such as HIGHPARON 20 (Trade name, produced by E. I. Du Pont de Nemours and Company). Such materials can be formed into an adhesive layer by dissolving the material in a solvent, directly applying to the first support layer or the first support layer and the second support layer and then drying. These materials may contain additives, such as crosslinking agents and flame retardants, for each purpose as required. Other examples of usable materials include acrylic resin adhesives, such as No. 500 (Trade name, produced by Nittoh Denko, Co., Ltd.), double-sided adhesive tapes such as A-10, A-20, A-30 (Trade name, produced by Three M Co., Ltd.), and silicone resin adhesives such as silicone adhesive sheet S9009 (Trade name, produced by Dow Corning Asia Co., Ltd.). These materials can be directly laminated on the first support layer or on the first adhesive layer and the second adhesive layer.

Examples of usable capillaries include commercially available glass capillaries. Preferred glass capillaries have, as an outermost layer, coating of a resin for glass protection. Suitable examples of such a resin include polyimide resin, silicone resin, fluorocarbon resin and epoxy resin. TSP, TSG and TSU (Trade name, produced by Polymicro Technologies Co., Ltd.) and capillary tubes produced by Moritex Co., Ltd. are examples of the glass capillaries having, as an outermost layer, coating of a resin for glass protection. The inside diameter and outside diameter of the capillaries may be selected depending on the purpose of usage.

According to the invention, a numerically controlled apparatus is used to lay a plurality of capillaries on the first adhesive layer. An example of the apparatus is disclosed in Japanese Patent Application Examined Publication No. S50-9346 (1975). The apparatus comprises a machining table for fixing thereon a pressure sensitive adhesive-clad base material by using riveting heads, a conductor wire feeding starter for feeding and laying a conductor wire on the base material into a desired line shape, and a cutter for cutting the conductor wire at a prescribed position. The apparatus is applicable to the method of the invention by replacing the conductor wire with a capillary, the adhesive-clad base material with a first support layer bearing a first adhesive layer. Laying the capillaries involves the problem that capillaries are easily broken on bending rapidly and sharply. A solution for laying capillaries without causing breakage nor leaving local stress is laying the capillaries to draw smooth circular arcs.

It is desirable the capillaries are preferably applied with a load while being laid on the first adhesive layer. It is also desirable the first adhesive layer and/or the capillaries are applied with energy convertible into heat while being laid on the first adhesive layer. For example, thermal energy can be applied by incorporating a heater inside the machining table for fixing the first support layer or by applying ultrasonic wave or by irradiating a laser ray to the capillaries or the first adhesive layer. The apparatus to be used is not limited.

The specifications of the sample injection portion 7 and the window portion 11 including sizes should be designed to fit the objective apparatus. At the sample injection portion 7 and the window portion 11, the first supporter A (that is, the first support layer 1, the first adhesive layer 2, the second adhesive layer 5 and the second support layer 6) is removed to expose the capillaries 4. The capillaries 4 exposed at the sample injection portion 7 and the window portion 11 should align in parallel at equal intervals. The capillaries should have equal distances between the terminating ends 8 in the sample injection portion 7 and the detection parts 9 defined as intersections of the capillaries 4 and a plane intersecting perpendicularly to the axes of the capillaries 4 in the window portion 11. The tolerance on the intervals and distances may be balanced with the measuring accuracy. Tolerance of ±0.5% or less is desirable for highly accurate measurements. The allowances may be larger when high accuracy is not required.

In general, the capillaries used have equal inside and outside diameters, and the intervals between the capillaries in the window portion 11 are desirably equal to the outside diameters of the capillaries, so that neighboring capillaries contact each other. The intervals between the capillaries at the sample injection portion 7 desirably are equal to those between wells containing a sample. It is also desirable to align the terminating ends 8 of the capillaries on one straight line.

When the capillaries used are covered with protecting coating, the coating layer in the window portion 11 should at least partially be peeled off not to intercept the irradiated light and excited light. Generally, it should be peeled off in a range of 1 to 5 mm at the detection parts 9, where the light is irradiated to and received. The value should be determined in accordance to the specifications of measuring apparatuses.

The first supporter may be removed at the window portion 11 and sample injection portion 7, for example, by peeling it off by hand labor, laser rays, or ozone asher or plasma asher disclosed in Japanese Patent Application Unexamined Publication No. 2002-082094. These means may be combined. Care should be taken in peeling by hand labor because excess force may be applied to disposition or break the capillaries. Laser light and ashers are particularly effective in keeping the capillary array accurate and preventing breakage. Laser rays, ozone ashing and plasma ashing are also applicable for peeling off the resin coating layer covering the capillary for protection.

Various ways may be employed to laminate the second support layer (in the embodiment of FIG. 1(4), the second support layer 6 bearing the second adhesive layer 5 on one surface). When a common pressing is employed, pressing conditions should be defined carefully to prevent the capillaries from breakage under high pressure. Vacuum lamination can prevent capillaries from being applied with high pressure and broken because pressing is carried out at lower pressure in a pre-vacuumed chamber.

The first supporter is then subjected to outside machining. The machining may be performed by cutting with a cutter or by pressing a metal cutting die shaped into the desired outside shape. Compared to cutters unsuitable to automation and cutting dies requiring much labor for production, preferred are numerically controlled laser machines, which require only the input of working data. As to laser machines, compared to high power machines specially designed for cutting, laser perforators of higher laser output per unit time, which have been recently used for printed wiring boards, are preferred to minimize scorching, because a point is perforated with a plurality of shots and the perforating point is moved repeatedly by about half the hole diameter.

The capillary electrophoresis apparatus of the invention comprises an electrophoresis member of one embodiment according to the invention wherein the first supporter has an opening including the window portion of the capillary layer, and a means for reflecting a laser ray in the opening to irradiate the laser ray to the detection parts of the capillaries through a plane parallel to the plane wherein the axes of the capillaries lie in parallel. The laser ray may be irradiated from one direction or from two opposed directions. For example, the means for reflecting a laser ray to the detection parts comprises a light source of the laser ray and at lease one mirror or prism arranged at least in the opening so as to reflect the laser ray irradiated from the light source. In the opening, only one mirror or prism may be arranged to face only one side of the parallel capillary array, or two may be arranged to face both sides respectively. The latter arrangement enables irradiating laser rays to the detection parts of the capillaries from two opposed directions. In this case, two light sources may be used, or a laser ray from one light source may be split by a beam splitter.

Analysis with the capillary electrophoresis of the invention is performed, for example, by further using a means for feeding a separation medium and a buffer, a means for applying voltage between both ends of each capillary fed with a separation medium and a buffer to drift the sample in the capillaries and a means for detecting the fluorescence emitted from the drifting sample by the irradiation of the laser ray.

The invention will be described in more detail with reference to the following Examples, which however are not to be construed to limit the scope of the invention.

EXAMPLES 1 AND 2

Example 1

FIG. 1 shows the production process employed in this example. CAPTON 300H (75 µm thick, trade name, produced by E. I. Du Pont de Nemours and Company) was used as the first support layer 1, and a silicone adhesive sheet S9009 (100 µm thick, trade name, produced by Dow Corning Asia Co., Ltd.) was used as the first adhesive layer 2 on one surface of the first support layer 1. A laying apparatus 3 (produced by Hitachi Chemical Co., Ltd.) that numerically controls applied load and the movement of an X-Y table was used to lay sixteen glass capillaries 4 (4-1–4-16) coated with polyimide resin (Trade name: TSP050150, produced by Polymicro Technologies Co., Ltd., outside diameter: 150 µm, inside diameter: 50 µm) on the first adhesive layer 2 so that the detection parts 9 were 20 cm distant from the terminating ends 8 of the sample injection portion 7. Load of 100 g was applied on the capillaries being laid. CAPTON 300H (75 µm thick, trade name, produced by E. I. Du Pont de Nemours and Company) was used as the second support layer 6, and a silicone adhesive sheet S9009 (100 µm thick, trade name, produced by Dow Corning Asia Co., Ltd.) was used as the second adhesive layer 5 on one surface of the second support layer 6. The second adhesive layer 5 and second support layer 6 were laminated on the laid capillaries 4 using a vacuum laminator. A laser perforator for perforating printed wiring boards with small-diameter holes were used for outside machining in the way that φ0.2 mm holes were made successively at intervals of 0.1 mm with four shots (pulse width: 5 ms) per hole. To expose the capillaries 4 at the window portion 11 including the detection parts 9 and at the sample injection portion 7 (FIG. 2), the first supporter A was cut without damaging the capillaries 4, and then the first support layer 1, the first adhesive layer 2, the second adhesive layer 5 and the second support layer 6 were peeled off by hands. The opening 11-2 measured 10 mm×20 mm in sizes. At a part 11-1 of the window portion including the detection parts 9, the polyimide coating layer covering the capillaries 4 was removed by a ozone asher.

In the product electrophoresis member, all the distances from the detection parts 9 and the terminating ends 8 in the sample injection portion 7 measured 20 cm±0.5 mm. The glass capillaries, at the window portion 11 including the detection parts 9, were aligned at intervals of 150 µm±10 µm, and at the sample injection portion 7, at intervals of 4.5 mm±0.1 mm. The capillaries were free of damage all over the laid area.

Figure 4:
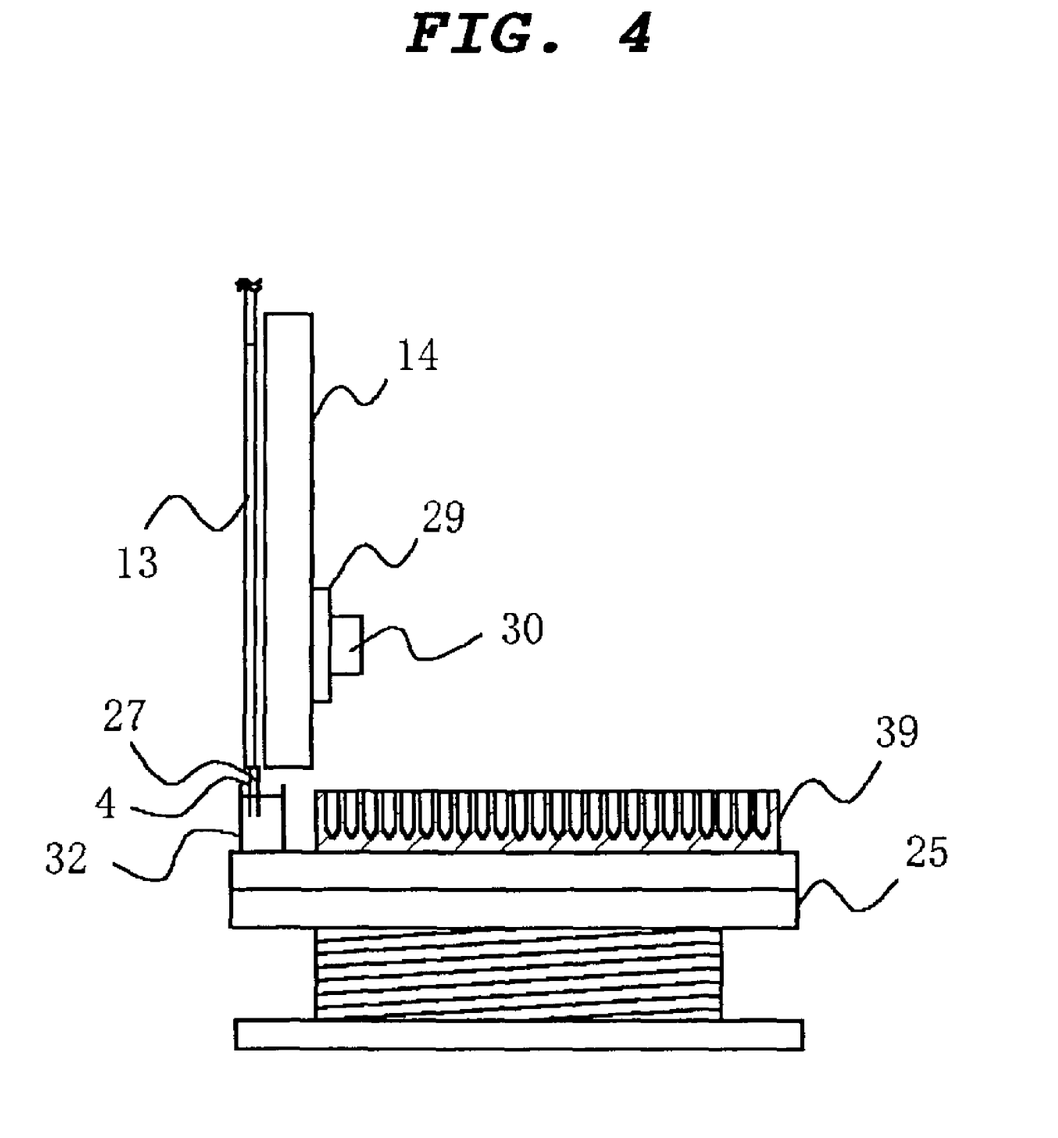
FIG. 4 is a right side view of the bulk of the electrophoresis apparatus of FIG. 3.
Figure 5:
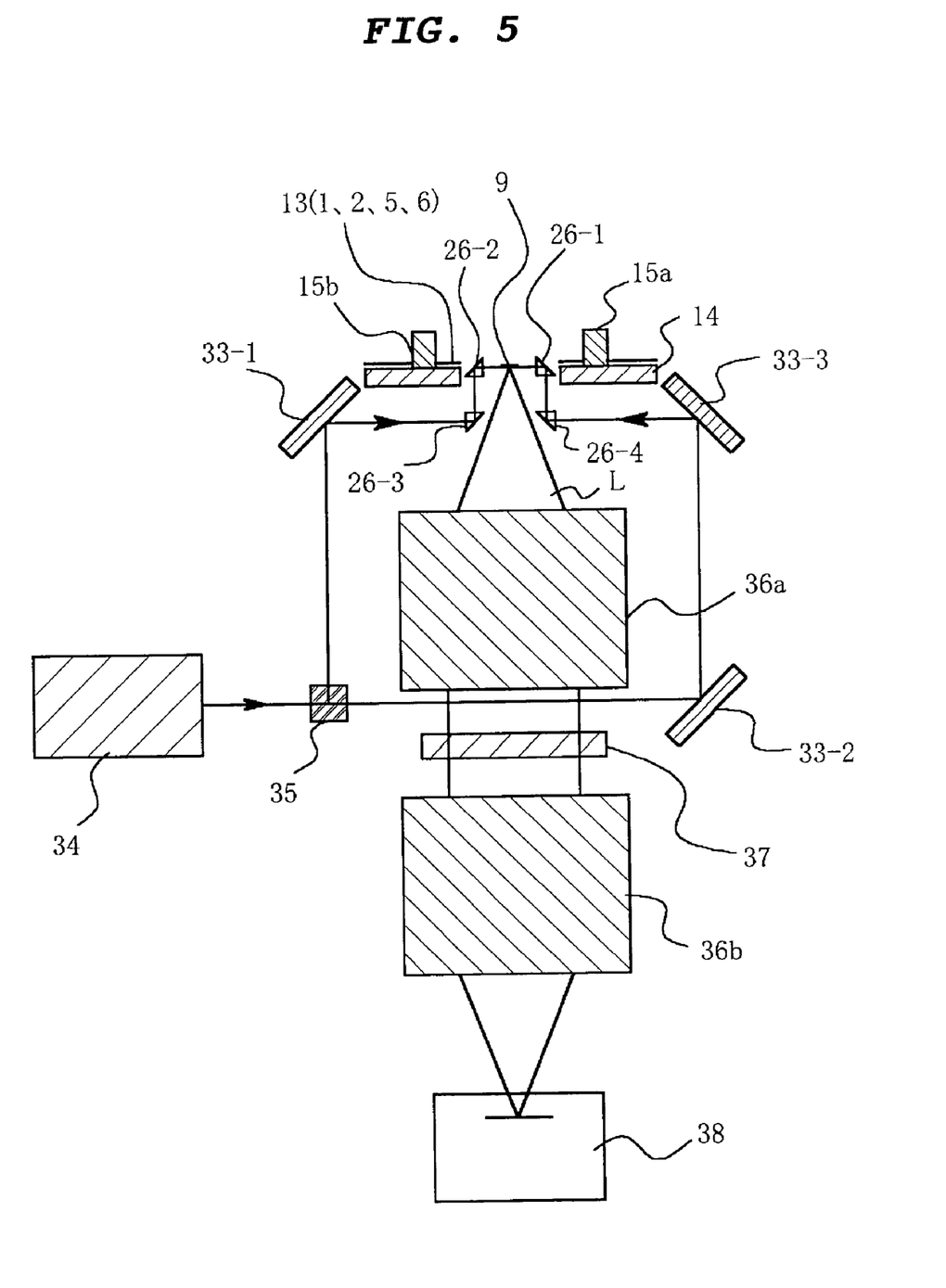
FIG. 5 is an X—X section of FIG. 3 illustrating an optical system for exciting and detecting fluorescence using the electrophoresis apparatus.

FIG. 2 is an elevation showing the product electrophoresis member, FIG. 3 is an elevation illustrating an electrophoresis system using the electrophoresis member, FIG. 4 is a side view showing the bulk of the electrophoresis system of FIG. 3, and FIG. 5 illustrates a measuring system using the electrophoresis system of FIG. 3.

As shown in FIG. 2, the first supporter A has the opening 11-2 including the window portion 11 of the capillaries 4. Holes 10a and 10b for setting up are made on both sides of the opening 11-2. In this example, the polyimide coating covering the capillaries 4 for protection was removed only at a part of the window portion 11-1 including the detection parts 9, but may be removed all over the window portion 11. At the detection parts 9 in the window portion 11, exciting light is irradiated to the sample drifting in the capillaries, and the resulting excited fluorescence is detected. In the window portion 11 and sample injection portion 7, the capillaries 4 (4-1–4-16) are arranged in the way their axes have a coplanar parallel relationship. One end portion of the first supporter A (the first support layer 1, the first adhesive layer 2, the second adhesive layer 5 and the second support layer 6) was removed to expose under the new edge the capillaries 4 to form the sample injection portion 7 of 10 mm length. The terminating ends 8 aligning on one line were made by cutting the capillaries 4-1–4-16. The sample in the microtiter plate 39 is injected into the capillaries 4-1–4-16 through the terminating ends 8. The upper edge of the first supporter A has a projection 12 only at the part where the capillaries 4 lie, to use the projection 12 for feeding a separation medium.

As shown in FIG. 3, the electrophoresis member 13 is accurately located and fixed by put the pins 15a and 15b fixed to a temperature control plate 14 through the holes 10a and 10b. The temperature control plate 14 is an aluminum plate having insulated surfaces and kept to a predetermined temperature by a Peltier element fixed to the backside. A heat pipe 30 and a fan 31 let the heat or cold generated by the Peltier element escape into a side direction and into the air.

The injection 12 of the electrophoresis member 13 is inserted into one channel of a diversion bloc 16 having a T-shaped channel, and is sealed by a rubber gasket. One of the remaining two channels in the diversion bloc 16 is connected through a tube 20 to a syringe 17 filled with a separation medium, the other through a tube 19 to a channel in a buffer block 18. The tube 19 and tube 20 are TEFLON (Trade name) tubes of 1 mm-inside diameter, and the diversion bloc 16 and buffer bloc 18 are made of a transparent acrylic resin, and the channels are 1 mm in inside diameter. The channel in the buffer bloc 18 is bent upward in the bloc and connected to a larger, crock-shaped buffer tank 18a. The connection part 18b between the channel in the buffer bloc 18 and the buffer tank 18a is opened and shut by the vertical motion of a piston 21. When the connection part 18b is opened, the syringe 17 is pushed to fill the separation medium into the tubes 19 and 20, the channel in the diversion bloc 16 connecting them and finally the channel in the buffer bloc 18. The buffer tank 18a has an upper open end, and a predetermined quantity of buffer is poured into therefrom. Thereafter, the piston 21 descends to shut the channel of the buffer bloc 18, and the syringe 17 is pushed again to fill now the separation medium into the capillary 4 of the electrophoresis member 13. The syringe 17 is pushed by an electromotive stage 24, and the piston 21 is vertically moved by an electromotive solenoid 22. Examples of suitable separation media are aqueous solution of acrylamide or hydroxyethyl cellulose. An example of a suitable buffer is an aqueous solution containing as main components tris(hydroxymethyl)aminomethane, boric acid and EDTA (hereinafter will be called TBE).

In a buffer bath 32, the lower ends of the capillaries 4 are dipped in the buffer together with an electrode 27 having sixteen projections paired. with the capillaries respectively. An electrode 23 is dipped in the buffer in the buffer bloc 18. High voltage is applied between the upper ends and lower ends of the capillaries 4 by a high tension power source 28 connected to electrodes 27 and 23.

As shown in FIG. 4, the buffer bath 32 and the microtiter plate 39 is placed on an X-Z stage 25. The X-Z stage 25 moves so that the lower ends of the capillaries 4 are dipped in the sample wells of the microtiter plate 39 and injected with the sample by the high tension power source 28, and then the terminating ends 8 of the sample injection portion 7 to conduct the electrophoresis separation of the sample in the capillaries 4 by applying high voltage between the upper ends and lower ends of the capillaries 4. Laser rays are irradiated through prisms 26-1 and 26-1 to the detection parts 9 of the capillaries 4 of the electrophoresis member 13 from two opposed directions perpendicular to the axes of the capillaries and in parallel to the plane on which the axes are arranged in parallel. At the time the drifting sample reached the detection parts 9 by electrophoresis, it is detected by the excitation of fluorescence.

All the procedures including filling the separation medium, injecting the sample and electrophoresis are automatically performed by computer control.

FIG. 5 is an X—X section of FIG. 3, illustrating the optical system assembled behind the temperature control plate 14 to excite and detect fluorescence. The light source 34 is a helium neon laser of 594 nm wavelength and 8 mW. The laser ray emitted from the laser is diverted into two by the beam splitter 35 and irradiated to both sides of the detection parts 9 by mirrors 33-1, 33-2, 33-3 and prisms 26-1-26-4. The laser ray transmitted through the beam splitter 35 is reflected by the prism 26-1 arranged in the opening 11-2 and irradiated to the detection parts 9 perpendicularly to the axes of the capillaries 4 from a direction parallel to the plane on which the axes are arranged in parallel. The laser ray reflected by the beam splitter 35 is irradiated through the prism 26-2 to the detection parts 9 of the capillaries from a direction opposed to the former laser ray. The laser rays irradiated to the outermost capillaries 4-1 and 4-16 are, as described in Japanese Patent Application Unexamined Publication No. H09-96623 (1997), irradiated to the adjacent capillaries successively by the lens effects of the capillaries without being made divergent. Irradiating from two opposed directions by diverting a laser ray into two cancels the loss due to reflection, and decreases the dispersion of the intensity of the laser ray to ±20% or less. The light L emitted by the sample from the capillaries 4 is made into a parallel beam by a camera lens 36a, and after the removal of background light other than the fluorescence of the sample by a band-pass filter 37, imaged in 1:1 by the second camera lens 36b on the photoelectric surface of an image pickup element 38. Because the image pickup element 38 pixel is a CCD of 25 μm in pixel pitch, it can separate and detect the fluorescence from each capillary 4.

Although a laser ray was diverted into two by the beam splitter 35 to irradiate the detection parts 9 of the capillaries from both sides in this example, irradiation from one side without the diversion of the laser ray is sufficient for lesser capillaries, such as four capillaries. In such a case, the beam splitter 35 may be replaced by a mirror, and the number of mirrors and prisms can be reduced to half.

Figure 6:
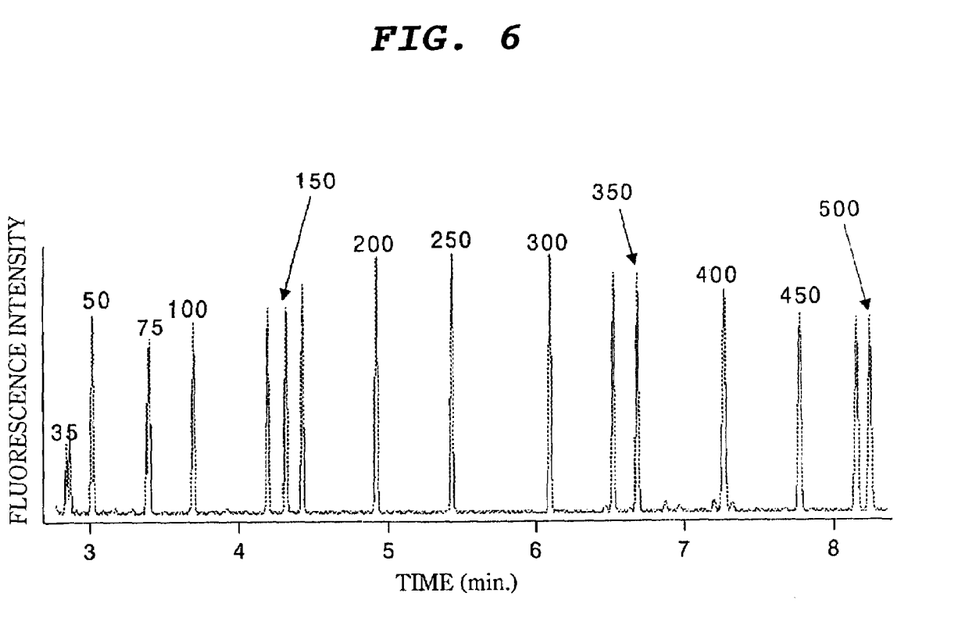
FIG. 6 is an electrophoresis chart obtained in Example 1.

FIG. 6 shows the changes of the intensity of the fluorescence from the capillaries with the passage of time obtained in this example. The sample used was GeneScan Size Standard 500 Rox (Trade name, produced by Applied Biosystems Co., Ltd.) containing DNA with ends within 500 bp labeled with ROX. The sample was diluted with formamide to ½₀ to make DNA into a single-stranded state, and injected into the capillaries 4. The numerical values over the peaks in FIG. 6 are the lengths of the bases corresponding to the peaks. The separation medium used was POP6 (Trade name, produced by the same company, acrylamide solution), the buffer used was TBE, and the electrophoresis electric field was 500 V/cm. Because of the high heat releasability of the electrophoresis member, a fine electrophoresis chart was obtained in a short time even with such a high electric field. In this example wherein the lengths of DNA fragments labeled with ROX are analyzed, sequencing by spectroscopic analysis of fluorescence using a diffraction grating in place of the band-pass filter is also applicable.

The capillaries in the sample injection portion are preferably spaced at intervals given by dividing 9 mm by an integer because the wells of the microtiter plate 39 is generally spaced at intervals given by dividing 9 mm by an integer. In this example wherein the integer is 2 and the intervals are 4.5 mm, a preferred is a microtiter plate with 384 wells. Of course, a microtiter plate with 96 wells may also be used by changing the integer to 1 to give intervals of 9 mm.

Example 2

Figure 8:
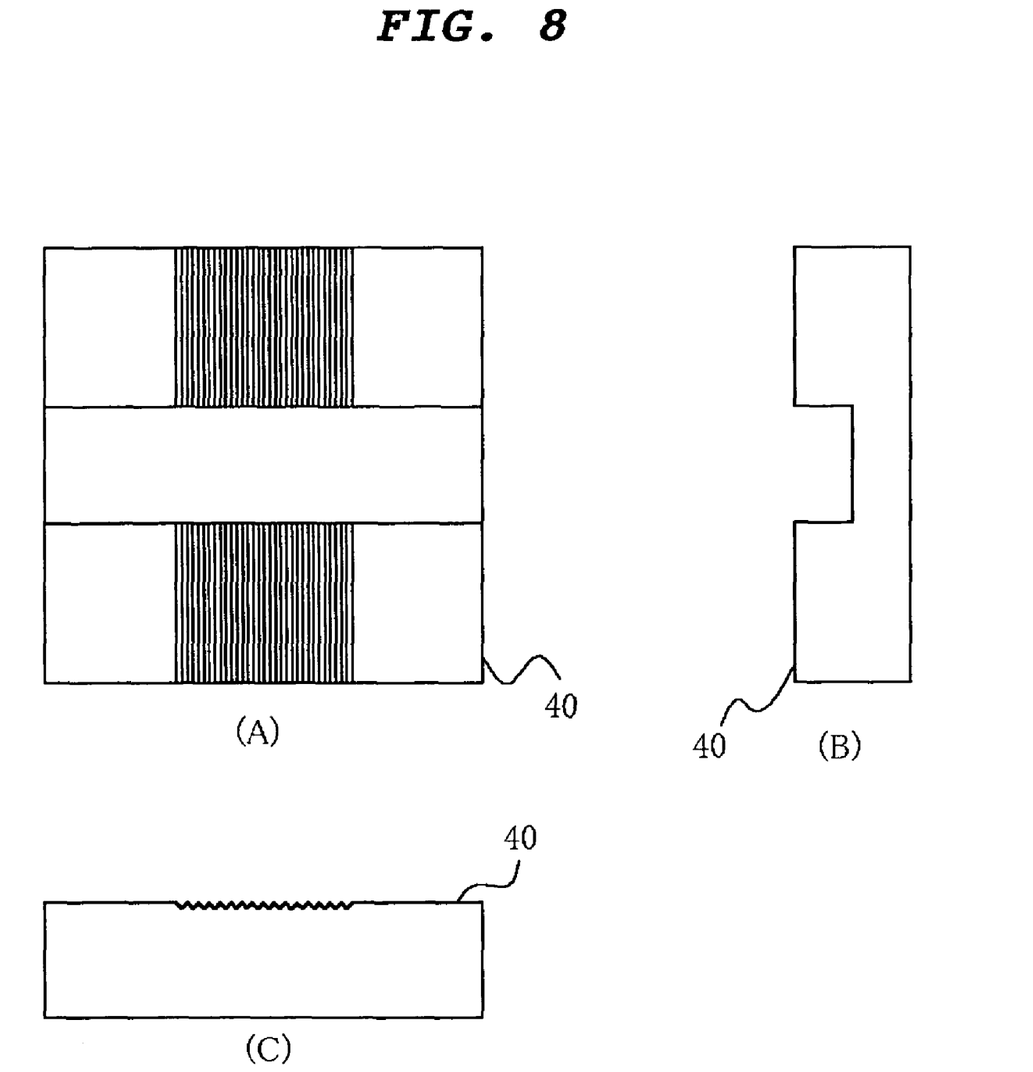
FIG. 8 shows enlarged views of the second supporter 40 shown in FIG. 7.

FIG. 7 shows an electrophoresis member of a second example according to the invention. In this example, the glass capillaries are supported before and behind the detection part 9 by a second supporter 40 (made of a plastic) having finely V-grooves for keeping the parallel capillary alignment. This made the intensity of the light irradiated to the capillaries more uniform to decrease its dispersion within ±10%. Further, the structure of the measuring system was simplified by removing the first support layer 1, the first adhesive layer 2, the second adhesive layer 5 and the second support layer 6 at all of the part opposing to the sample injection portion 7 of the capillaries 4 and including the detection parts 9. 41 is a cylindrical ferrule having a penetrating hole. The capillaries are bundled and inserted into the hole, and gaps are filled with an adhesive. The cylindrically bundled ends of the capillary array allow easy sealing, enabling filling the electrophoresis medium in a shorter time by applying higher pressure. FIG. 8 is an enlargement of the second supporter 40, wherein (A) is an elevation, (B) is a side view and (C) is a bottom view. As shown in FIG. 8, the second supporter 40 has sixteen V-grooves, and a square groove is made at the part where the detection parts 9 are placed, not to intercept the irradiation.

As described above, according to the invention, there are provided an electrophoresis member wherein capillaries are aligned accurately and an efficient method of producing the electrophoresis member. Further, the most part of capillaries in the electrophoresis member is shielded from the air to improve the heat-releasing efficiency, allowing very high speed analysis with higher voltage gradient compared to the conventional capillary arrays.

What is claimed is:

1. An electrophoresis member, comprising a plurality of capillaries and a first supporter comprising a first support layer, a first adhesive layer and a second support layer, wherein:

the first adhesive layer is positioned on the first support layer, the capillaries lie on the first adhesive layer to form a capillary layer, and the second support layer is positioned on the capillary layer;

the capillary layer has a window portion and a sample injection portion including a terminating end of each capillary, the capillaries, at the sample injection portion, being exposed by partially removing one end portion of the first supporter and, at the window portion, being exposed by partially removing another portion of the first supporter;

the capillaries, at each of the window portion and the sample injection portion, are arranged so that axes of the capillaries have a parallel, coplanar relationship;

the capillaries have, in the window portion, detection parts defined as intersections of the capillaries and a plane intersecting perpendicularly to the axes of the capillaries; and the capillaries have equal lengths between the detection parts and the terminating ends included in the sample injection portion.

2. The electrophoresis member of claim 1, wherein the capillaries are glass capillaries.

3. The electrophoresis member of claim 1, wherein the first supporter has a second adhesive layer interposed between the capillary layer and the second support layer.

4. The electrophoresis member of claim 1, wherein each capillary, except the window portion or a part of the window portion including the detection part, has a coating layer as an outermost layer.

5. The electrophoresis member of claim 1, wherein the capillaries, at the sample injection portion, are arranged at equal intervals given by dividing 9 mm by an integer.

6. The electrophoresis member of claim 1, wherein the capillaries, in the window portion, are supported before and behind the detection parts by a second supporter.

7. The electrophoresis member of claim 1, wherein the first supporter has an opening including the window portion.

8. A capillary electrophoresis apparatus, comprising the electrophoresis member of claim 7 and a means for reflecting a laser ray in the opening to irradiate the laser ray to the detection parts of the capillaries through a plane parallel to the plane wherein the axes of the capillaries lie in parallel.

9. A method of producing an electrophoresis member, comprising steps (1), (2) and (3):

(1) a step of forming a capillary layer comprising a plurality of capillaries on an adhesive layer born on a first support layer, by laying the capillaries on the adhesive layer by using a numerically controlled laying apparatus, so that the capillary layer has a window portion and a sample injection portion including a terminating end of each capillary, the capillaries, at each of the window portion and the sample injection portion, being arranged so that axes of the capillaries have a parallel, coplanar relationship;

the capillaries have, in the window portion, detection parts defined as intersections of the capillaries and a plane intersecting perpendicularly to the axes of the capillaries; and the capillaries have equal lengths between the detection parts and the terminating ends included in the sample injection portion;

(2) a step of laminating a second support layer on the capillary layer; and (3) a step of exposing the capillaries, at each of the window portion and the sample injection portion, by partially removing the first support layer, the first adhesive layer and the second support layer.

10. The method of claim 9, wherein, in step (2), the second support layer bears on one surface a second adhesive layer, and is laminated on the capillary layer, so that the second adhesive layer contacts the capillary layer, and, in step (3), the capillaries, at each of the window portion and the sample injection portion, are exposed by partially removing the first support layer, the first adhesive layer, the second adhesive layer and the second support layer.

11. The method of claim 9, wherein the capillaries are glass capillaries.

12. The method of claim 9, wherein each capillary is a glass capillary having a coating layer as an outermost layer, and the method further comprises a step of peeling off the coating layer at the window portion or at a part of the window portion including the detection parts.

13. The method of claim 9, wherein the capillaries are applied with a load while being laid on the first adhesive layer.

14. The method of claim 9, wherein the first adhesive layer and/or the capillaries are applied with energy convertible into heat while being laid on the first adhesive layer.

* * * * *